(12) United States Patent
Bohannon

(10) Patent No.: US 6,210,677 B1
(45) Date of Patent: Apr. 3, 2001

(54) METHOD TO REDUCE THE PHYSIOLOGIC EFFECTS OF DRUGS ON MAMMALS

(76) Inventor: Robert C. Bohannon, 11851 Acadian, Houston, TX (US) 77099

( * ) Notice: Subject to any disclaimer, the term of this patent is extended or adjusted under 35 U.S.C. 154(b) by 0 days.

(21) Appl. No.: 09/112,065

(22) Filed: Jul. 7, 1998

Related U.S. Application Data

(63) Continuation of application No. 08/203,002, filed on Feb. 28, 1994, now abandoned, and a continuation-in-part of application No. 08/010,903, filed on Jan. 29, 1993, now abandoned.

(51) Int. Cl.[7] ................................................. A61K 39/385
(52) U.S. Cl. .................................. 424/193.1; 424/196.11; 424/197.11
(58) Field of Search ........................... 424/184.1, 193.1, 424/196.11, 197.11

(56) References Cited

U.S. PATENT DOCUMENTS

| | | | |
|---|---|---|---|
| 4,235,864 | * 11/1980 | Kaul et al. | 424/1 |
| 4,620,977 | * 11/1986 | Strahilevitz | 424/88 |
| 5,773,003 | * 6/1998 | Swain et al. | 424/193.1 |

FOREIGN PATENT DOCUMENTS

WO 92/03163   3/1992   (WO) .

OTHER PUBLICATIONS

Bagasra, et al., Immunopharmacology, 23:173–179, Jun. 1992.*
Carrera et al., Nature, 378:727–730, Dec. 1995.*
Gallacher, G., Immunopharmacology, 27:79–81, Feb. 1994.*
Okawa, et al., Journal of Immunological Methods, 149:127–131, 1992.*

* cited by examiner

Primary Examiner—Donna C. Wortman
Assistant Examiner—Brenda G. Brumback
(74) Attorney, Agent, or Firm—Townsend and Townsend and Crew, LLP

(57) ABSTRACT

A method to reduce the physiologic effects of drugs in vivo by inducing specific anti-drug antibodies using drugs conjugated to carrier molecules so as to reduce a drug's toxicity and its physiologic effects upon the recipient. This method includes the treatment and prophylactic prevention of drug abuse, specifically for cocaine and nicotine, and to help reduce the toxic effects of drugs, such as anti-neoplastics.

8 Claims, 1 Drawing Sheet

METHOD TO REDUCE THE PHYSIOLOGIC EFFECTS OF DRUGS ON MAMMALS

This application is a continuation division of and claims the benefit of U.S. application Ser. No. 08/203,002, filed Feb. 28, 1994, now abandoned and a continuation-in-part of U.S. application Ser. No. 08/010,903, filed Jan. 29, 1993, now abandoned the disclosure of which are incorporated by reference.

FIELD OF THE INVENTION

This invention relates to a method for reducing the physiologic effects of drugs on mammals in vivo. Specifically, the method of this invention consists of inducing specific anti-drug antibodies in mammals with immunogens consisting of a drug conjugated to a carrier molecule. More particularly, the method of this invention consists of generating antibodies towards addictive substances—particularly cocaine and nicotine—such that the physiologic effects of such addictive substances are reduced. As a result, toxicity to such addictive substances is dramatically lowered in those mammals which have been treated with the immunogens prior to introduction of the addictive substance. In addition, mammals can be afforded prophylactic protection from such addictive substances by the administration of the drug-conjugated immunogen prior to introduction of the addictive substance.

BACKGROUND OF THE INVENTION

The National Institute of Drug Abuse National Household Survey on drug abuse estimated that in 1991 there were approximately 12 million persons in the United States that abused drugs. This included approximately 4.5 million occasional abusers of cocaine and greater than 800,000 habitual users of cocaine. The United States government is projected to spend an estimated $12 billion in 1993 on federal drug control programs with an estimated $2.7 billion allocated to help defray the cost of drug treatment programs. Typical methods of drug treatment therapy include psychological counseling. Heroin addiction is sometimes treated with methadone therapy to permit gradual withdrawal, however, the replacement drug methadone is itself addictive.

It would be highly desirable to develop a method to neutralize or minimize the effects of controlled substances or addictive drugs thereby rendering continued abuse of addictive substances unproductive due to the reduced physiologic effect of the drug on the user. Additionally, a physiologic reduction of the action of the drug, or reduction of the rate in which the drug effects the mammalian subject, would help contribute to reduce the toxicity of the drug. Such a method would be highly desirable in the treatment of habitual substance abusers, in the prophylactic prevention of abuse, to reduce toxicity of drugs, and may provide an additional method to slowly release toxic anti-neoplastic drugs.

SUMMARY OF THE INVENTION

The present invention consists of the administration of an immunogen consisting of a drug conjugated to a carrier molecule. The immunogen induces in the recipient the production of antibodies to the drug, as well as to the carrier molecule in most cases. Such antibodies, in turn, sequester a subsequently administered drug thereby reducing the drug's physiologic effects in the recipient. To demonstrate the method of this invention, an anti-cocaine immunogen was synthesized that markedly demonstrated a reduction in the physiologic effects and toxicity of cocaine in laboratory animals. A "reduction in the physiologic effect of a drug" is defined herein as that which can be readily observed and measured, such as heart rate, breathing rate, auditory stimulus, eye dilation, irritability, agitation, and pain reflex, in the case of cocaine.

The present invention describes a method for preventing or treating drug abuse by administering drug-conjugated immunogen that induces in the recipient antibodies, which specifically recognize and neutralize a targeted controlled substance. Such antibodies are then available in the treated recipient to reduce or eliminate the effect of a subsequent intake of the drug including reduction of the physiologic effects of subsequent drug use and reduction of the toxicity of the drug. The invention therefore is of great assistance in drug treatment programs.

The method of this invention may also be employed to reduce anti-neoplastic drug toxicity and to provide for a method of slow in vivo release of drugs.

DETAILED DESCRIPTION OF THE PREFERRED EMBODIMENT

Figure 1:
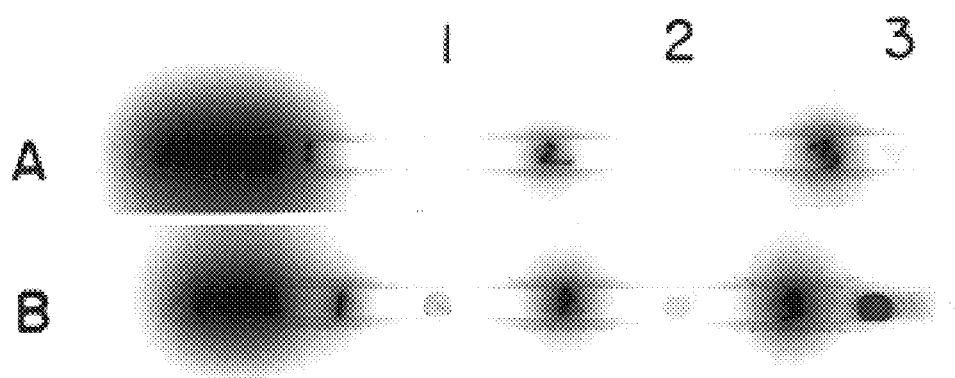
FIG. 1 is an immunoblot showing reactivity of cocaine-conjugated immunogens with antisera of an animal treated with the anti-cocaine immunogen.

The drug-conjugated immunogen of the present invention is a substance which induces in a mammal the production of antibodies which minimize or neutralize the effect of a targeted controlled substance or drug. Antibodies against addictive substances, drugs, or anti-neoplastic compounds also reduce the toxic effects of the respective drug by keeping the blood level of unbound drugs in the bloodstream at a relatively low level while the drug is cleared-by enzymes, the reticulo-endothelial system, the liver, secreted via the kidneys, or other methods used in mammals to dispose or clear toxic substance. The ability of the drug-conjugated immunogen to reduce such toxic effects thereby minimizes the likelihood of a drug overdose. Toxicity resulting in death, seizure and tissue damage is greatly diminished thereby.

A controlled substance or drug is defined herein to include those substances known to be subject to abuse, e.g., cocaine, morphine (opium), heroin, and tetrahydrocannabinol (marijuana). Additional substances included in the invention are those which are habit forming such as various pain relievers, stimulants, anti-depressant drugs and nicotine. These substances, as well as other drugs which are potential candidates for abuse or that are toxic, are contemplated as targets for the drug-conjugated immunogen and method of the present invention, and are thus to be included in the definition of "controlled substances" or "drugs" for purposes of the present invention.

Anti-cocaine immunogens and a method to treat cocaine abuse are exemplified herein, but it is understood that the immunogen and method of the present invention may similarly be applied to other controlled substances or drugs. The method of the invention reduces the toxicity of drugs—due to antibody sequestering of the target drug induced by the drug-conjugated immunogen—and thus provides a method of releasing toxic drugs, such as anti-neoplastic compounds, into the bloodstream of the host mammal, thereby slowly reducing the side-effects of toxic compounds or drugs.

Cocaine, most controlled substances, and anti-neoplastic drugs are compounds having low molecular weights and do not tend to elicit an effective immune response when injected into mammals. However, cocaine, controlled substances, and anti-neoplastic compounds may be conjugated to carrier molecules. The resulting conjugate is of sufficient size and thus becomes immunogenic so as to generate an immune response, thereby producing antibodies against the drug of the conjugate.

Carrier molecules suitable for conjugation with controlled substances and drugs that would generate an immunogen include, for example, sheep albumin, polysaccharide such as mannan, and various lipopolysaccharides such as those derived from *Salmonella typhosa*. Many conventional carriers known to those skilled in the art may also be used in this invention, including those approved by regulated governmental agencies for use in humans, such as, for example: Diphtheria, Tetanus, and Pertussis vaccines or components thereof; poliovirus vaccines and components thereof; Rubella, Mumps, and Measles vaccines or components thereof; Hepatitis vaccines (A,B,C, and delta) and components thereof; Haemophilus (A and B) vaccines and components thereof; vaccinia and smallpox vaccines and components thereof; varicella-zoster vaccines and components thereof, as well as synthetic multiple antigenic peptides (MAPs) and derivatives thereof.

The conjugation method used will depend upon the chemistry of coupling a particular drug to a particular carrier. Suitable agents and methods for conjugating a variety of compounds are commercially available from Pierce Chemical Co. (Rockford, Ill.), as described, for example in the Pierce Chemical Co. catalog. Known methods for conjugating two or more compounds via specific reactive groups may be applied to the preparation of the drug-carrier molecule conjugates of the present invention. In general, a reactive site on a first compound is linked to a reactive site on a second compound, using a coupling agent or catalyst.

Coupling agents include EDC (1-ethyl-3-(3-dimethylaminopropyl) carbodiimide-HCL, (Pierce Chemical Company, Catalog No. 22980), glutaraldehyde and other similar agents. (See, for example, Axen et al., *Nature*, 214:1302–1987; and Okawa et al., *Journal of Immunological Methods*, 149:127, 1992).

The compound conjugated to the carrier may be a natural or synthetic drug, controlled substance, anti-neoplastic compound, or a derivative thereof. For example, the cocaine derivative benzoylecgonine was used to form a drug-carrier conjugate which induces the production of antibodies against cocaine in a recipient.

The drug-carrier conjugate may contain a drug to carrier ratio of 1:1 or greater, e.g., 75:1, depending upon available conjugation sites on the carrier molecule. In some cases, a polymeric carrier may be used which may carry a large number of drug molecules, e.g., greater than 100:1 drug-:carrier.

The drug-conjugated immunogens of the present invention are immunogenic. A particular drug-conjugated immunogen may be tested for immunogenicity, for example, by immunization of test animals and analysis of the resulting antisera. A drug-conjugated immunogen may be modified to make the composition more immunogenic. Such modifications includes conjugation to lipopolysaccharides, synthetic peptides, or to molecules which stimulate the immune system.

The drug-carrier conjugate immunogens of the present invention are administered to a recipient by known, conventional methods, e.g., injection, inhalation, or by oral delivery, depending upon the physiological characteristics of the drug and carrier compounds. Preferably, the agent is administered by subcutaneous injection. The conjugate is prepared in a pharmaceutically acceptable carrier, for example, in an aqueous medium such as water, buffer, saline, glycine, or an oil based carrier, as appropriate for the specific drug-carrier conjugate and the desired mode of delivery.

A therapeutically effective dose of the drug-conjugated immunogen is administered to a recipient mammal, e.g., human, rabbit, monkey or mouse. A therapeutically effective dose of the drug-conjugated immunogen is one that induces in the recipient the production of antibodies to the desired drug or controlled substance, which antibodies are effective to reduce or eliminate a response to a subsequent challenge or intake of the controlled substance, anti-neoplastic agent, or drug. It is understood that a single administration or multiple administrations of the drug-conjugated immunogen may be required to induce adequate antibody titres, depending upon each recipient's immune competence. In general, one to four injections will be used.

Successful immunization of the recipient may be monitored, for example, by analyzing the ability of a recipient's anti-serum to bind the controlled substance or drug of choice. Immunoassay methods such as ELISA and immunoblot may be used for such analysis. Immunized mammals, when presented with a challenge dose of controlled substance or drug, exhibit diminished effects or no effect of the controlled substance or drug.

The method of the present invention may be used to immunize mammals, including rabbits and humans, against controlled substances and other drugs as a method of preventing or treating drug abuse or to reduce a drug's toxic effects. Immunization against such drugs as cocaine, heroin, opium, morphine, marijuana, nicotine, and anti-neoplastic compounds should reduce or nullify the physiologic effects of these drugs in the recipient and thereby help to reduce the drug's toxicity.

The invention may be better understood by reference to the following examples:

EXAMPLE 1

Preparation of a Benzoylecgonine-Conjugated Immunogen

To form a conjugate between benzoylecgonine, a cocaine derivative, and sheep albumin, 5 mg of sheep albumin was conjugated to 1 mg of benzoylecgonine using 100 mg of EDC (1-ethyl-3-(3-dimethylaminopropyl) carbodiimide-HCl, Pierce Chemical Company, Catalog No. 22980) in 1 ml of 0.1 M MES buffer (2-(N-morpholino)ethanesulfonic acid) at pH 4.5 for four hours at 50° C. The mixture was dialyzed against water for two days at room temperature using a 1,000 m.w. cutoff dialysis tubing. Approximately 5 mg of the benzoylecgonine-albumin conjugated immunogen (COALB) in a volume of 1.5 ml was recovered and used in the subsequent studies.

Similarly, conjugates of benzoylecgonine to mannan or lipopolysaccharide were formed by dissolving 10 mg of mannan (Sigma Chemical Co. #M7504) or *Salmonella typhosa* lipopolysaccharide (Sigma Chemical Co. #L6386) in 0.1 M sodium carbonate-buffer, pH 10.7, to which 10 mg of cyanobromide (CNBr) was added in a volume of 1 ml. The mixture was allowed to react for ten minutes at room temperature. Diaminopropane (50 μl) was added and the mixture was allowed to sit overnight at room temperature. This process provided amine groups on the polysaccharide for coupling of benzoylecgonine. The mixture was dialyzed with water overnight using a 1000 molecular weight cutoff dialysis membrane to yield activated polysaccharide. To 5 mg of the activated polysaccharide in 0.9 ml volume was added 5 mg of benzoylecgonine in 50 µl of 30% ethanol followed by the addition of 50 mg of EDC in 50 µl of 0.5 M MES buffer at pH 4.5. This solution was incubated at 50° C. for a period of four hours then dialyzed against water for 24 hours using 1000 molecular weight cutoff dialysis membrane. Approximately 5 mg of each conjugate, benzoylecgonine-mannan (COMAN) and benzoylecgonine-lipopolysaccharide (COLPS) in a volume of 1.5 ml was recovered and used in the subsequent studies.

EXAMPLE 2

Conjugation of Bensoylecgonine to Diphtheria Toxin

Similarly benzoylecgonine can be coupled to other carrier molecules such as Diphtheria Toxin. In this example, 5 mg. of Diphtheria toxin (Sigma D7544) is dissolved in 0.9 ml of 0.1M MES (pH 4.5) to which is added 1 mg. of benzoylecgonine dissolved in a volume of 0.5 ml. 0.1M MES (pH 4.5) and to which 10 mg. EDC in 0.5 ml of 0.1M MES (pH 4.5) is added. This coupling reaction is performed at 50° C. for four hours then the mixture is dialyzed against water or PBS using a 1000 molecular weight cut-off dialysis membrane or purified by passing the mixture over an gel filtration column. The recovered conjugate can then be used as drug-conjugated immunogen.

EXAMPLE 3

Preparation of Anti-Neoplastic-Conjugated Immunogens

Anti-neoplastic drugs, or other highly toxic drugs, may be directly coupled to carrier molecules as a method to lower the toxicity of the drug and to provide controlled release or degradation of the drug. For example, methotrexate can also be coupled to albumin, diphtheria toxoid, tetanus toxoid, and modified polysaccharide as described above. In this example, 5 mg. of a carrier molecule, which has amine groups for binding, such as tetanus toxoid, is coupled to 1 mg. of methotrexate in 0.9 ml of 0.1M MES (pH 4.5) to which is added 10 mg. of EDC dissolved in 1 ml of 0.1M MES (pH 4.5). The mixture is allowed to couple the anti-neoplastic, or other toxic substance, to the carrier molecule—tetanus toxoid in this example—for four hours at 50° C. after which the drug-conjugated immunogen is purified by dialyzing against water or a buffered solution, such as PBS, or is purified by column filtration or by High Pressure Liquid Chromatography. The resulting drug-conjugated immunogen elicits an immune response in a mammal thereby generating antibodies against the conjugated agent:methotrexate.

EXAMPLE 4

Immunization with Benzoylecgonine-Conjugated Immunogen

Two rabbits were immunized with the cocaine-conjugated immunogen COALB, prepared as described for Example 1. Rabbits were immunized with COALB by subcutaneous injection of 100 µg of the benzoylecgonine-conjugated immunogen every two weeks for a period of two months (four injections). Freund's complete adjuvant was used in the first injection and Freund's incomplete adjuvant was utilized for subsequent injections.

To test for the presence of anti-cocaine antibodies, the serum of the treated rabbits was analyzed by immunoblot assay for its ability to bind the benzoylecgonine conjugates produced in Example 1.

Approximately 1 µg of each drug-carrier conjugated immunogen was spotted onto nitrocellulose strips and allowed to air dry. These strips were blocked for one hour at room temperature using 1:10 Mega-block I (ONASCO Products, Houston, Tex.).

Sera obtained from the test rabbits both before and after immunization with COALB were diluted 1:100 in the blocking solution and applied to the test strips. After incubating for two hours at room temperature, the strips were washed four times in a solution of saline and 0.01% tween-20 and the secondary antibody was added (1:1000 dilution of goat anti-rabbit antibody conjugated with alkaline phosphatase, in 1:100 Mega-block I blocking buffer). The strips were incubated for two hours at room temperature then washed four times in 0.01% tween-20 solution. Bound antibodies were detected by reacting the substrate NBT/BCIP (Promega Biotech) with the bound secondary antibody which resulted in a visually detectable signal.

The results of this immunoblot assay are shown in FIG. 1, where strip A shows rabbit sera prior to immunization and strip B shows rabbit sera after four doses of the COALB. The COMAN (1), COLPS (2) and COALB (3) immunogens each reacted with antibody present in the rabbit sera after immunization. The background signal in the pre-immunization COALB (3) spot is expected due to the nature of the albumin carrier.

The immunized rabbits were then challenged with an intravenous dose of cocaine-HCl (Sigma Chemical Co., #C5776) in sterile saline at 2 mg/kg wt ($LD_{50}$ of 12 mg/kg). Control rabbits challenged with the same dose of cocaine showed marked grande maul convulsions, involuntary eye movements, rapid and shallow breathing, were unresponsive to both visual, auditory, and pain stimuli, had dilated eyes, but recovered after 10–15 minutes. Clearly, the i.v. administered cocaine caused pronounced physiologic effects upon the animals and nearly caused the death of one of the animals due to the drug's toxic effects upon the rabbit. Two rabbits immunized with the COALB immunogen, when injected with the same dose of cocaine (2 mg/kg), showed none of the dramatic effects that the control rabbits had demonstrated. The treated animals remained responsive, and no physiologic effects of the cocaine injection were noted, which clearly demonstrated that the anti-cocaine immunogen, COALB, was effective in suppressing the physiologic effects of the cocaine challenge as well as apparently lowering the drugs toxicity as demonstrated by the lack of physiologic trauma when compared to an un-immunized animal.

EXAMPLE 5

Immunization with Benzoylecgonine-Conjugated Immunogen

In a similar fashion, anti-benzoylecgonine immunogens described above in Example 2 (those conjugated to diphtheria or tetanus toxoid) are used to immunize mammals other than rabbits (such as monkeys and humans) to suppress the action of cocaine and its derivatives upon the central nervous system and to increase tolerance of the mammal to the drug. One hundred µg of the anti-cocaine immunogen is absorbed to an approved adjuvant aluminum hydroxide and is injected s.c. Similarly, anti-neoplastic or anti-toxic conjugates could be used as drug-conjugated immunogens in this example.

EXAMPLE 6

Preparation of a Nicotine-Conjugated Immunogen

Nicotine (3-1-Methyl-2-pyrrolidinyl)pyridine; 1-methyl-2-(3-pyridyl)pyrrolidine; beta-pyridyl-alpha-N-methyl-pyrrolidine) is conjugated to a carrier molecule (albumin, cationized albumin, amine-linked mannan, amine-linked polysaccharide, diphtheria toxoid, tetanus toxoid, or other such molecules) using the PharmaLink Immunogen Kit commercially available from Pierce Chemical Company, Rockford, Ill. catalog number 77158 G. Following the instructions provided, nicotine-HCl is dissolved in the conjugation buffer which includes the carrier compound, Super-Carrier. The coupling agent provided in the Pierce kit is then added and the mixture is incubated for 2 to 24 hours at approximately 37–57° C. (The time required is related to the temperature of incubation.) The resulting conjugate is then purified from non-conjugated nicotine using a desalting column.

Alternatively, approximately 1 mg of carrier protein, e.g. tetanus or diphtheria toxoid, is dissolved in 200 μl of 0.1 M MES buffer, pH 4.5, 0.15M NaCl, and approximately 1 mg. of nicotine-HCl in 200 Ml of 0.1 M MES buffer, pH 4.5, 0.15 M NaCl is added. A volume of 50 μl of 37% formaldehyde is added next and the mixture is allowed to react at 37° C. for approximately 3 hours. The solution is dialyzed overnight against water using a 1000 m.w. cutoff membrane.

The resulting nicotine-carrier conjugated immunogen is then used to immunize a recipient, following the procedures for Example 2.

EXAMPLE 7

Immunization with Nicotine-Conjugated Immunogen

Humans and monkeys are immunogenized with anti-nicotine immunogens wherein the conjugated immunogen is absorbed onto a pharmaceutically approved adjuvant aluminum hydroxide and injected i.m. using a dose which causes the generation of relatively high titre antibodies (100 μg–500 μg). Several injections may be required before suitable antibody titres are obtained.

In a similar fashion, toxic compounds, such as anti-neoplastic agents, are coupled to carrier molecules using the same method of coupling via a condensation reaction to active hydrogen molecules.

One mg. of a carrier molecule, such as sheep albumin, is dissolved in 0.2 ml. of 0.1 M M-ES (pH 4.5) and 0.15 M NaCl. to which 1 mg. of vinblastine dissolved in .2 ml of ethanol is added followed by the addition of 0.5 ml. of 37% formaldehyde. The condensation-coupling reaction is allowed to proceed at 37° C. for 3 hours after which the mixture is dialyzed, or otherwise purified, to remove the salts, buffering agents, formaldehyde and unbound vinblastine. The immunogen is then used to generate antibodies towards vinblastine by immunizing a mammal (mouse, rabbit, monkey, or human) so as to lower the drug's toxicity during treatment in the same manner as described above.

EXAMPLE 8

Preparation of Morphine-Conjugated Immunogen

Morphine (7,8-Didehydro-4,5-epoxy-17-methyl-morphinan-3,6-diol) is conjugated to albumin, mannan, or lipopolysaccharide using conjugation methods as described for Examples 1 and 6. Approximately 5 mg of morphine acetate-trihydrate (Sigma Chemical Co.) is dissolved in 0.5 ml of 0.1 M MES, pH 4.5. To this is added approximately 5 mg of sheep albumin dissolved in 0.45 ml of 0.11 MES, pH 4.5. EDC, 50 mg in 50 μl of 0.1 M MES, pH 4.5 is added and the mixture reacted for approximately 4 hours at 50° C. The resultant conjugate is dialyzed against water overnight at room temperature, changing water approximately every 2 hours and using a 1000 m.w. cutoff membrane.

The resultant morphine-conjugated immunogen is used to immunize mammals (rabbits, mice, monkeys, or humans) as described in Example 2. The resulting antibodies to morphine sequester morphine, and derivatives thereof, thereby suppressing its effects upon the central nervous system and thereby reducing the toxicity of the drug.

What is claimed is:

1. A method for suppressing or reducing in mammals the physiological effects caused by cocaine comprising:

administering to a mammal, prior to the administration of the cocaine. an immunogen which consists of cocaine or a cocaine derivative conjugated to a carrier molecule; and inducing in the recipient the production of anti-cocaine antibodies wherein physiological effects of the cocaine are suppressed by the antibodies upon subsequent exposure of the mammal to cocaine.

2. The method of claim 1 wherein the immunogen is a cocaine derivative.

3. The method of claim 2, wherein the cocaine derivative is benzoylecgonine.

4. The method of claim 1, wherein the carrier molecule is selected from the group consisting of albumin, polysaccharide, and lipopolysaccharide.

5. The method of claim 4, wherein the polysaccharide is mannan.

6. The method of claim 1, wherein the carrier molecule is an antigenic protein.

7. The method of claim 4, wherein the immunogen is cocaine or a cocaine derivative.

8. The method of claim 7, wherein the polysaccharide is mannan.

* * * * *